United States Patent [19]
Lurie et al.

[11] Patent Number: 6,155,257
[45] Date of Patent: Dec. 5, 2000

[54] CARDIOPULMONARY RESUSCITATION VENTILATOR AND METHODS

[75] Inventors: Keith G. Lurie; Todd M. Zielinski, both of Minneapolis, Minn.

[73] Assignee: CPRx LLC, Minneapolis, Minn.

[21] Appl. No.: 09/168,049

[22] Filed: Oct. 7, 1998

[51] Int. Cl.$^7$ .................................................. A61M 16/00
[52] U.S. Cl. ............................. 128/204.23; 128/204.18; 128/205.24; 600/534
[58] Field of Search ..................... 128/204.23, 204.18, 128/204.24, 204.28, 205.13, 205.14, 205.16, 205.24; 600/534, 538

[56] References Cited

U.S. PATENT DOCUMENTS

| | | | |
|---|---|---|---|
| 2,774,346 | 12/1956 | Halliburton | 128/29 |
| 3,191,596 | 6/1965 | Bird et al. | 128/29 |

(List continued on next page.)

FOREIGN PATENT DOCUMENTS

| | | |
|---|---|---|
| 668771 | 8/1963 | Canada . |
| 2 077 608 | 3/1993 | Canada . |
| 0 029 352 A1 | 5/1981 | European Pat. Off. . |
| 0 367 285 A2 | 5/1990 | European Pat. Off. . |
| 0 411 714 A1 | 2/1991 | European Pat. Off. . |
| 0 509 773 A1 | 10/1992 | European Pat. Off. . |
| 1 465 127 | 11/1974 | United Kingdom . |
| 2 139 099 | 11/1984 | United Kingdom . |
| WO 90/05518 | 5/1990 | WIPO . |
| WO 93/21982 | 11/1993 | WIPO . |
| WO 94/26229 | 11/1994 | WIPO . |
| WO 95/13108 | 5/1995 | WIPO . |
| WO 95/28193 | 10/1995 | WIPO . |
| WO 96/28215 | 9/1996 | WIPO . |

OTHER PUBLICATIONS

Geddes, L.A., "Electrically Produced Artificial Ventilation," *Medical Instrumentation* 22(5): 263–271 (1988).

Glenn, William W.L., et al., "Twenty Years of Experience in Phrenic Nerve Stimulation to Pace the Diaphragm," *Pace* 9: 780–784 (Nov./Dec. 1986, Part I).

Kotze, P.L. et al., "Diaphragm Pacing in the Treatment of Ventilatory Failure," *Sant. Deel* 68:223–224 (Aug. 17, 1995).

Geddes, L.A. et al., "Inspiration Produced by Bilateral Electromagnetic, Cervical Phrenic Nerve Stimulation in Man," *IEEE Transactions on Biomedical Engineering* 38(9): 1047–1048 (Oct. 1991).

Geddes, L.A. et al., "Optimum Stimulus Frequency for Contracting the Inspiratory Muscles with Chest Surface Electrodes to Produce Artificial Respiration," *Annals of Biomedical Engineering* 18:103–108 (1990).

(List continued on next page.)

*Primary Examiner*—John G. Weiss
*Assistant Examiner*—V. Srivastava
*Attorney, Agent, or Firm*—Townsend and Townsend and Crew LLP

[57] ABSTRACT

The invention provides systems and methods for ventilating a patient in association with cardiopulmonary resuscitation procedures. In one exemplary embodiment, a system comprises a ventilator to periodically supply respiratory gases to a patient's lungs. A sensor is provided to detect chest compressions by sensing changes in intrathoracic pressure. A controller is coupled to the sensor and controls actuation of the ventilator after a predetermined number of chest compressions have been detected by the sensor.

53 Claims, 14 Drawing Sheets

U.S. PATENT DOCUMENTS

| | | | |
|---|---|---|---|
| 3,307,541 | 3/1967 | Hewson | 128/204.18 |
| 3,509,899 | 5/1970 | Hewson | 128/204.18 |
| 3,662,751 | 5/1972 | Barkalow et al. | 128/145.8 |
| 3,669,108 | 6/1972 | Sundblom et al. | 128/145.8 |
| 3,794,043 | 2/1974 | McGinnis | 128/349 BV |
| 3,815,606 | 6/1974 | Mazal | 128/351 |
| 3,834,383 | 9/1974 | Weigl et al. | 128/145.8 |
| 3,973,564 | 8/1976 | Carden | 128/204.23 |
| 4,041,943 | 8/1977 | Miller | 128/145.8 |
| 4,077,404 | 3/1978 | Elam | 128/145.8 |
| 4,166,458 | 9/1979 | Harrigan | 128/24 R |
| 4,226,233 | 10/1980 | Kritzer | 128/205.13 |
| 4,259,951 | 4/1981 | Chernack et al. | 128/200.14 |
| 4,262,667 | 4/1981 | Grant | 128/204.21 |
| 4,298,023 | 11/1981 | McGinnis | 137/529 |
| 4,316,458 | 2/1982 | Hammerton-Fraser | 128/205.24 |
| 4,397,306 | 8/1983 | Weisfeldt et al. | 128/28 |
| 4,446,864 | 5/1984 | Watson et al. | 128/207.14 |
| 4,449,526 | 5/1984 | Elam | 128/206.21 |
| 4,533,137 | 8/1985 | Sonne | 272/99 |
| 4,601,465 | 7/1986 | Roy | 272/99 |
| 4,809,683 | 3/1989 | Hanson | 128/28 |
| 4,827,935 | 5/1989 | Geddes et al. | 128/419 |
| 4,881,527 | 11/1989 | Lerman | 128/30.2 |
| 4,928,674 | 5/1990 | Halperin et al. | 128/30.2 |
| 5,014,698 | 5/1991 | Cohen | 128/419 |
| 5,050,593 | 9/1991 | Poon | 128/204.23 |
| 5,109,840 | 5/1992 | Daleiden | 128/205.13 |
| 5,163,424 | 11/1992 | Kohnke | 128/205.13 |
| 5,184,620 | 2/1993 | Cudahy et al. | 128/639 |
| 5,193,544 | 3/1993 | Jaffe | 128/634 |
| 5,235,970 | 8/1993 | Augustine | 128/200.26 |
| 5,301,667 | 4/1994 | McGrail et al. | 128/205.14 |
| 5,305,743 | 4/1994 | Brain | 128/207.15 |
| 5,355,879 | 10/1994 | Brain | 128/207.15 |
| 5,359,998 | 11/1994 | Lloyd | 128/203.11 |
| 5,392,774 | 2/1995 | Sato | 128/207.15 |
| 5,454,779 | 10/1995 | Lurie et al. | 601/43 |
| 5,492,116 | 2/1996 | Scarberry et al. | 128/206.24 |
| 5,496,257 | 3/1996 | Kelly | 601/41 |
| 5,517,986 | 5/1996 | Starr et al. | 128/206.24 |
| 5,551,420 | 9/1996 | Lurie et al. | 128/205.13 |
| 5,584,866 | 12/1996 | Kroll et al. | 607/5 |
| 5,645,522 | 7/1997 | Lurie et al. | 601/43 |
| 5,692,498 | 12/1997 | Lurie et al. | 128/205.24 |
| 5,730,122 | 3/1998 | Lurie | 128/207.12 |
| 5,735,876 | 4/1998 | Kroll et al. | 607/5 |
| 5,738,637 | 4/1998 | Kelly et al. | 601/41 |
| 5,782,883 | 7/1998 | Kroll et al. | 607/14 |
| 5,806,512 | 9/1998 | Abramov et al. | 128/204.18 |
| 5,814,086 | 9/1998 | Hirschberg et al. | 607/14 |
| 5,823,185 | 10/1995 | Chang | 128/204.18 |

OTHER PUBLICATIONS

Laghi, Franco et al., "Comparison of Magnetic and Electrical Phrenic Nerve Stimulation in Assessment of Diaphragmatic Contractility," *American Physiological Society*, pp.1731–1742 (1996).

Glenn, William W.L. et al., "Diaphragm Pacing by Electrical Stimulation of the Phrenic Nerve, " *Neurosurgery* 17(6): 974–984 (1985).

Dupuis, Yvon G., "Ventilators Theory and Clinical Application," *Mosby Company* 1986.

Ambu International A/S, "Directions for Use for Ambu CardioPump".

Cohen et al. (1992) "Active Compression–Decompression Resuscitation: A Novel Method of Cardiopulmonary Resuscitation" American Heart Journal 126(5): 1145–1150.

Cohen, Todd J. et al., "Active Compression–Decompression: A New Method of Cardiopulmonary Resuscitation," *JAMA* 267(21): 2916–2923 (Jun. 3, 1992).

Lindner, Karl H. et al., "Effects of Active Compression–Decompression Resuscitation on Myocardial and Cerebral Blood Flow in Pigs" *Department of Anesthesiology and Critical Care Medicine, University of Ulm, Germany* (Oct. 7, 1993).

Lurie, Keith G. et al., "Regulated to Death: The Matter of Informed Consent for Human Experimentation in Emergency Resuscitation Research," *Cardiac Arrhythmia Center at the University of Minnesota* 18:1443–1447 (Jul. 1995).

CARDIOPULMONARY RESUSCITATION VENTILATOR AND METHODS

BACKGROUND OF THE INVENTION

1. Field of the Invention

The present invention relates generally to the field of cardiopulmonary resuscitation. In particular, the invention relates to devices and methods for ventilating a patient in association with cardiopulmonary resuscitation procedures.

Worldwide, sudden cardiac arrest is a major cause of death and is the result of a variety of circumstances, including heart disease and significant trauma. In the event of a cardiac arrest, several measures have been deemed to be essential in order to improve a patient's chance of survival. These measures must be taken as soon as possible to at least partially restore the patient's respiration and blood circulation. One common technique, developed approximately 30 years ago, is an external chest compression technique generally referred to as cardiopulmonary resuscitation (CPR). CPR techniques have remained largely unchanged over the past two decades.

With traditional CPR, pressure is applied to a patient's chest in order to increase intrathoracic pressure. An increase in intrathoracic pressure induces blood movement from the region of the heart and lungs towards the peripheral arteries. Such pressure partially restores the patient's circulation. Traditional CPR is performed by actively compressing the chest by direct application of an external pressure to the chest. After active compression, the chest is allowed to expand by its natural elasticity which causes expansion of the patient's chest wall. This expansion allows some blood to enter the cardiac chambers of the heart. The procedure as described, however, is insufficient to ventilate the patient. Consequently, conventional CPR also requires periodic ventilation of the patient. This is commonly accomplished by mouth-to-mouth technique or by using positive-pressure devices, such as a self-inflating bag which relies on squeezing an elastic bag to deliver air via a mask, endotracheal tube or other artificial airway.

In order to increase cardiopulmonary circulation induced by chest compression, a technique referred to as active compression-decompression (ACD) has been developed. According to ACD techniques, the active compression phase of traditional CPR is enhanced by pressing an applicator body against the patient's chest to compress the chest. Such an applicator body is able to distribute and apply force substantially evenly over a portion of the patient's chest. More importantly, however, the applicator body is sealed against the patient's chest so that it may be lifted to actively expand the patient's chest during the decompression step. The resultant negative intrathoracic pressure induces venous blood to flow into the heart and lungs from the peripheral venous vasculature of the patient.

Other techniques for increasing cardiopulmonary circulation while performing CPR include impeding airflow into the patient's lungs during decompression of the patient's chest. Such techniques are described in U.S. Pat. Nos. 5,551,420 and 5,692,498, and in copending U.S. patent application Ser. No. 08/950,702. The complete disclosures of these references are herein incorporated by reference. In one particular embodiment, airflow into the patient's chest is impeded by placing a pressure-responsive valve in the patient's airway. The valve prevents the flow of air into the patient's lungs during the decompression phase until a threshold negative intrathoracic pressure is reached. At this point, the valve opens to allow airflow to the patient's lungs. Hence, when the valve is closed, the amount of negative intrathoracic pressure is increased, thereby enhancing the amount of venous blood flow to the heart and lungs.

When performing CPR, there is a need to periodically ventilate the patient. Some common techniques include mouth-to-mouth ventilation, ventilatory bags, and ventilation machines. However, as of yet there has been no effective and convenient way to coordinate the timing of ventilation with the chest compressions. For example, if mouth-to-mouth resuscitation is provided, the rescuer must count each chest compression, stop chest compressions when a predetermined number of chest compressions have been performed, manually ventilate the patient with the rescuer's mouth, and then return to performing chest compressions. Similar problems are experienced when using ventilatory bags. Moreover, with many manual ventilation techniques, it is difficult, if not impossible, to precisely control the timing and volume of air delivered to the patient.

Hence, it would be desirable to provide methods and devices for ventilating a patient in association with cardiopulmonary resuscitation procedures. It would be particularly desirable to provide a way to easily and conveniently coordinate the timing of chest compressions with ventilation. It would be further desirable to precisely control the volume of respiratory gases delivered to the patient.

2. Description of the Background Art

U.S. Pat. Nos. 5,551,420 and 5,692,498, previously incorporated by reference describe techniques for preventing airflow to the patient's lungs during the decompression phase of CPR.

ACD-CPR techniques are described in detail in Todd J. Cohen et al., *Active Compression-Decompression Resuscitation: A Novel Method of Cardiopulmonary Resuscitation*, American Heart Journal, Vol. 124, No. 5, pp. 1145–1150, November 1992; and Todd J. Cohen et al., *Active Compression-Decompression: A New Method of Cardiopulmonary Resuscitation*, The Journal of the American Medical Association, Vol. 267, No. 21, Jun. 3, 1992. These references are hereby incorporated by reference.

The use of a vacuum-type cup for actively compressing and decompressing a patient's chest during ACD-CPR is described in a brochure of AMBU International A/S, Copenhagen, Denmark, entitled Directions for Use of AMBU® CardioPump™, published in September 1992. The AMBU® CardioPump™ is also disclosed in European Patent Application No. 0 509 773 A1. These references are hereby incorporated by reference.

SUMMARY OF THE INVENTION

The invention provides exemplary systems and methods for ventilating a patient in association with cardiopulmonary resuscitation procedures. In one exemplary embodiment, a ventilation system comprises a ventilator to periodically supply respiratory gases to a patient's lungs and a sensor to detect chest compressions. A controller is coupled to the sensor and controls actuation of the ventilator after a predetermined number of chest compressions have been detected by the sensor. Hence, such a system provides a convenient and easy way to coordinate ventilation with chest compressions by simply sensing when the patient's chest has been compressed and periodically ventilating the patient after a predetermined number of chest compressions have been detected. Preferably, the controller is configured to actuate the ventilator to supply respiratory gases to the patient once about every 2 to about 10 chest compressions, with adults typically receiving about one ventilation for about every 5 chest compressions.

The invention includes various ways to detect when the patient's chest has been compressed. For example, in one particularly preferable aspect, the system includes a valve which is placed in the patient's air way. The sensor is disposed so as to be able to detect the flow of respiratory gases through the valve upon compression of the chest. In this manner, an easy way is provided to detect chest compressions simply by sensing the flow of respiratory gases through the valve. In one particular aspect, the sensor comprises a strain gauge that is strained as respiratory gases flow through the valve, and a resistance sensing circuit to sense a change in resistance of the strain gauge when strained. Such a sensor is particularly advantageous when the valve includes a diaphragm, such as the diaphragms provided in the threshold negative intrathoracic pressure valves described in U.S. Pat. Nos. 5,551,420 and 5,692,498, previously incorporated herein by reference. When the diaphragm moves due to gases exiting the patient, the strain gauge is strained.

Other techniques for detecting chest compressions include sensing intrathoracic pressure changes in the patient's airway, sensing when an external force has been applied to the patient's chest, such as with a load cell or strain gauge positioned on the patient's chest, by sensing an impedance change in the chest wall, and the like. Sensors that may be employed to detect such parameters include pressure sensors, piezoelectric sensors, spirometers, thermistors, pneumotachometers, capacitative sensors, and the like.

During at least a portion of the decompression phase, respiratory gases are preferably prevented from entering into the patient's lungs. An occlusion mechanism is preferably employed to occlude the patient's airway during the desired portion of the decompression phase. The occlusion mechanism may be adjustable so that it will open at a pre-set pressure level. In this way, when a threshold negative intrathoracic pressure level is reached or exceeded during decompression, the occlusion mechanism is actuated to allow respiratory gases to enter into the patient's lungs.

Actuation of the occlusion mechanism may be directly caused by the negative intrathoracic pressure within the patient, such as with a threshold valve as described in U.S. Pat. Nos. 5,551,420 and 5,692,498, may be controlled by the controller based on information received from a pressure sensor disposed in the patient's airway, or may be actuated by the controller at delayed time intervals after a chest compression has been sensed. In the event that a sensor detects that spontaneous breathing has occurred, the controller may be configured to operate the occlusion mechanism so that respiratory gases are free to flow to the patient's lungs. Other exemplary occlusion mechanisms that may be employed by the invention include airways that are closed using a rotary cam wheel, using a linear actuator with a compression member or a pair of caliper arms, and the like.

In one particular aspect, chest compressions are performed manually. Alternatively, chest compressions may be performed using an automated compression mechanism, such as the one described in U.S. Pat. No. 4,397,306, the complete disclosure of which is herein incorporated by reference.

In another particular aspect, the ventilator comprises a compressible member, such as a bag, and a compression mechanism to compress the member. Alternatively, a cylinder with a piston may be employed. In this way, the amount of respiratory gases supplied to the patient may be precisely controlled by controlling the amount of compression of the member or the size of the cylinder and the stroke of the piston. As such, ventilation based upon either a preset volume or a preset pressure can be delivered with the ventilator.

In another aspect, the controller includes a timing circuit that may be employed to regularly actuate the ventilator during times when regular chest compressions are not being performed. In this way, the patient may be ventilated once CPR is stopped. In still another aspect, the system further includes a power supply to supply power to the controller and the ventilator. In this way, the system may be configured to be portable so as to facilitate its use in emergency procedures.

In yet another aspect, the system includes at least one feedback sensor that is coupled to the controller. The feedback sensor provides feedback to the rescuer regarding various physiological parameters. For example, the sensor may comprise an oxygen sensor, a carbon dioxide sensor, a temperature sensor, a chest compression force sensor, a depth of chest compression sensor, a chest compression pressure sensor, a pH sensor, and the like. Optionally, actuation or timing of the ventilator may be based on the state of the various physiological parameters.

In still yet another exemplary aspect, the system includes a control panel having a mode control to change the operational mode of the ventilator. As one example, the mode control may include a compression detect mode where the ventilator is actuated after a predetermined number of chest compressions have been detected by the sensor. The mode control may also include a manual ventilation mode where the patient may be manually ventilated by operating a ventilation switch on the control panel. Still further, the mode control may include an automatic ventilation mode as previously described so that the patient may be ventilated at regularly timed intervals when chest compressions are not being performed.

The control panel may also include a threshold compression control which is used to vary the sensitivity level of the sensor. The control panel preferably also includes an air volume control to control the volume of respiratory gases supplied by the ventilator upon each actuation. The air volume control may also be used to control the mix of oxygen and air, e.g., 21%–100% $FiO_2$. The air volume control may also be employed to control the pressure of respiratory gases supplied to the patient. Optionally, the control panel may further include a compression counter display which displays the number of detected chest compressions. A compression detector display may also be provided to display when each chest compression has been detected. Still further, the control panel may include a ventilation indicator to indicate when the ventilator is actuated. The control panel may also indicate the amount of pressure or force applied to the chest. This may be accomplished by displaying a number or a waveform demonstrating changes in compression, force, or pressure over time.

In another exemplary embodiment, the invention provides a method for performing cardiopulmonary resuscitation. According to the method, a patient's chest is repeatedly compressed. Each chest compression is detected using a sensor which is coupled to a controller. The patient is periodically ventilated after a predetermined number of chest compressions have been detected. In this way, the timing of patient ventilation may be coordinated with the number of chest compressions by sensing changes in intrathoracic pressure that are caused by chest compression.

Detection of chest compressions may be performed in a variety of ways. For example, chest compressions may be detected by sensing changes in intrathoracic pressure, by sensing air flowing through the patient's airway, by sensing when an external force is applied to the patient's chest, by sensing impedance changes in the chest wall, and the like. In one particular aspect, the change in intrathoracic pressure is sensed by placing a valve in the patient's airway and sensing when respiratory gases flow through the valve.

In one particular aspect, respiratory gases are prevented from flowing to the lungs with the valve until a threshold negative intrathoracic pressure is exceeded, at which time the valve opens to allow the respiratory gases to flow to the lungs. In another alternative, respiratory gases are prevented from flowing to the lungs using other occlusion mechanisms which operate based on signals received from the controller. In this way, the controller may be employed to operate the occlusion mechanisms when it is desired to allow respiratory gases to flow to the lungs.

In another aspect, a compressible bag is mechanically compressed to ventilate the patient. The bag may be automatically compressed after a predetermined number of chest compressions have been detected, or may be manually actuated by the rescuer. In one aspect, compression of the patient's chest is stopped after cardiac function has been restored, and the patient is ventilated at regular intervals.

In still yet another aspect, at least one physiologic parameter is sensed while performing chest compressions. Such parameters may include, for example, oxygen, carbon dioxide, temperature, pH, and the like. The timing of ventilations may be based on the state of one or more of these parameters. Conveniently, a visual signal may be produced when each chest compression has been detected. In another option, the number of chest compressions may be counted and displayed for viewing by the rescuer. Also, an indicator may be visually displayed each time the patient is ventilated.

In yet another embodiment, the invention provides an exemplary ventilation device which comprises a compressible bag and a mechanical compression mechanism which may be operated to compress the bag. A coupling member is attached to the bag to couple the bag to a patient's airway.

In one particular aspect, the mechanical compression mechanism comprises a plunger having a rack, a stepping motor, and a pinion coupled to a motor to move the rack. Alternatively, the compression mechanism may comprise a plunger and a compressed air cylinder to move the plunger. Preferably, a threshold valve is disposed in the coupling member and is configured to open when experiencing a threshold negative intrathoracic pressure.

DETAILED DESCRIPTION OF THE SPECIFIC EMBODIMENTS

Figure 1:
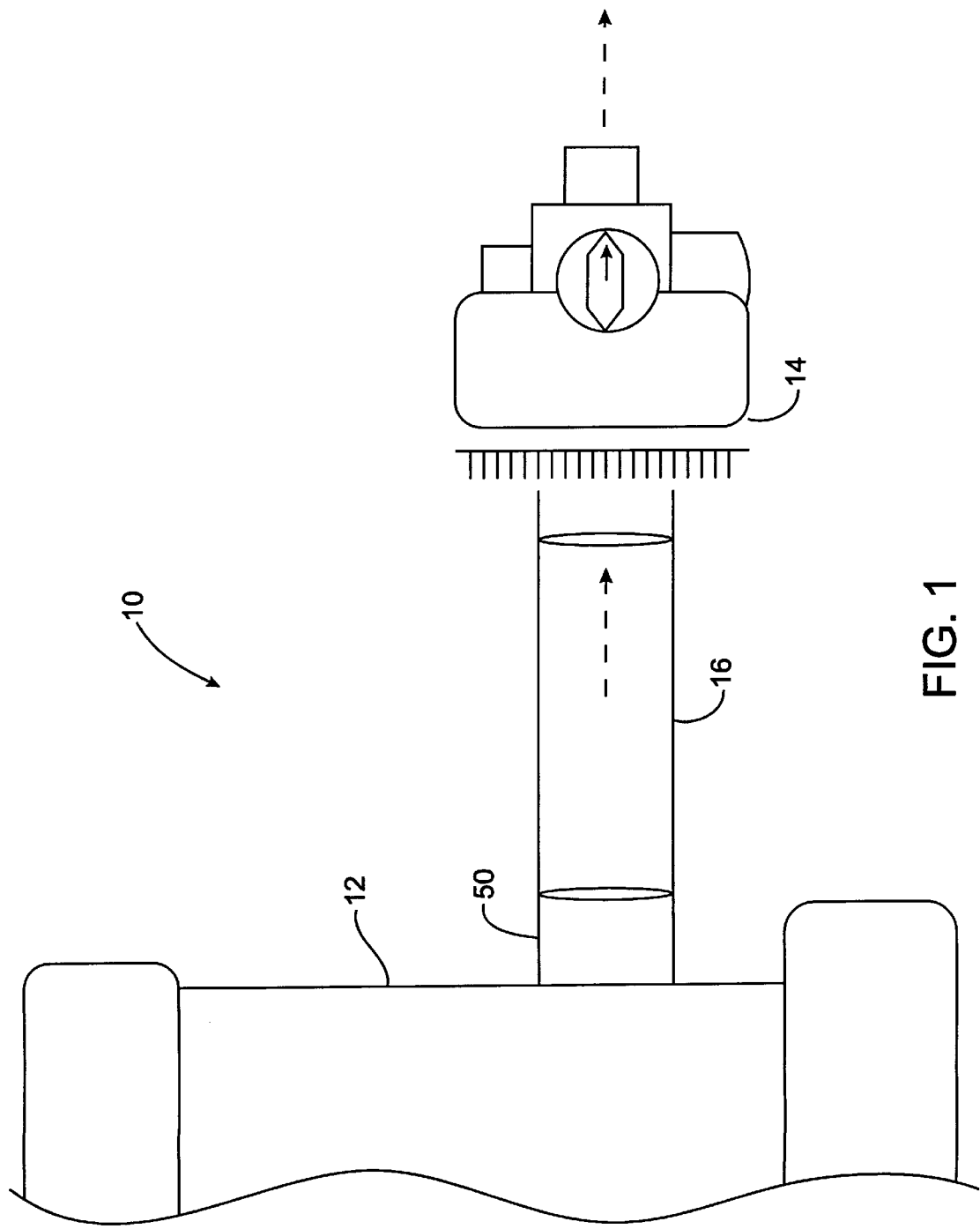
FIG. 1 is a schematic view of an exemplary ventilator which is coupled to a valve having a sensor to detect chest compressions by sensing changes in intrathoracic pressure according to the invention.

The invention provides exemplary systems and methods for ventilating a patient in association with cardiopulmonary resuscitation procedures. In a broad sense, the invention provides for the coordination of patient ventilation with chest compressions. Such coordination is preferably accomplished by sensing each time the chest is compressed and counting the number of compressions. After a predetermined number of compressions have been performed, a ventilator is actuated to ventilate the patient. Preferably, chest compressions are sensed by detecting a change in intrathoracic pressure while performing CPR. Each time the patient's chest is compressed, the intrathoracic pressure in the patient significantly increases. Such an increase may be detected and related to a chest compression.

In one particularly preferable aspect, the change in intrathoracic pressure is sensed by detecting the flow of respiratory gases from the patient's lungs during chest compressions. One particularly preferable way to detect when respiratory gases exit the patient's lungs is by placing a valve in the patient's airway and detecting the flow of respiratory gases through the valve. As one example, the valve may comprise a threshold valve having a diaphragm which opens when respiratory gases exit the patient's lungs as described generally in U.S. Pat. Nos. 5,551,420 and 5,692,498, previously incorporated by reference. A sensor, such as a strain gauge, pressure sensor, optical sensor, or the like, may be disposed in the valve to detect when the diaphragm opens. Information from the sensor is then employed to count the number of chest compressions. Another sensor that may be employed to detect a change in intrathoracic pressure is a pressure sensor that is disposed in the patient's airway. Other sensors that may be employed to detect when the chest has been compressed include sensors which directly detect when an external force is applied to the chest. For example, a compression pad which is placed on the patient's chest may include a sensor, such as a strain gauge or a load cell, which generates a signal each time the pad is compressed. These signals are sent to the controller to actuate the ventilator. As another example, the compression pad may be filled with fluid. A pressure transducer may then be employed to detect when the pad has been compressed. As another alternative, a change in impedance of the chest wall may be sensed to indicate that the chest has been compressed.

The ventilators of the invention are preferably configured to supply a precise amount of respiratory gases to the patient's lungs during each delivery. In one particularly preferable embodiment, the proper volume of respiratory gases are produced by compressing a compressible bag by a known amount. For example, a plunger may be moved against the compressible bag by a known distance to produce a precise amount of respiratory gases.

In another particularly preferable embodiment, the proper volume of respiratory gases are administered to the patient by utilizing a pressure sensing mechanism disposed within the patient's airway. The tidal volume and flow of respiratory gases are automatically determined by the amount of positive inspiratory pressure supplied to the patient's airway. The sensing mechanism, such as a pressure sensor disposed within the airway, senses the amount of positive pressure in the airway during the inspiratory cycle of ventilation and maintains the positive pressure through a feedback control mechanism. In this mechanism, the airway pressure is held constant throughout the inspiratory period and the timing of breaths administered can be determined by a controlled preset rate. This mechanism is advantageous to accommodate changes in patient lung compliance and decrease the overall work of ventilation during CPR.

In another particularly preferable embodiment, a preset volume of respiratory gas is administered to the patient at a specified timing interval. If the patient spontaneously breaths or gasps within the timing interval of no ventilation, the ventilator automatically senses the spontaneous breath utilizing a pressure sensing mechanism disposed in the ventilatory circuit, and initiates an inspiratory ventilation cycle to assist the patient's breath attempt. The ventilator timing cycle then resets to the preset value and ventilates the patient at the determined timing cycle or on the next spontaneous breath by the patient. If a predetermined number of spontaneous breaths have been detected within a preset timing window, the ventilator automatically switches to a stand-by mode to allow the patient to spontaneously breathe independent of the ventilator. The patient then breathes gas with the same temperature, humidity, and oxygen concentration, as the ventilator would provide through a parallel ventilatory circuit. If the ventilator detects that a spontaneous breath has not been initiated within a predetermined timing window, the ventilator automatically switches from stand-by mode to active mode and beings to ventilate the patient at the specified timing interval. This mechanism is advantageous for patients who begin to initiate spontaneous breathing during CPR and provides a positive pressure breath to be administered synchronously with the patient's spontaneous ventilatory pattern or, while in stand-by mode, weans the patient from ventilatory assist to independent breathing.

The ventilators of the invention are preferably configured to include a rechargeable power supply so that the ventilators may be transported to any given location where medical assistance is needed. In some cases, the compressible bag may be configured to be removed from the ventilator so that manual ventilation may be performed as desired.

When performing cardiopulmonary resuscitation, it is desirable to have the ventilator actuated once about every 2 to about 10 chest compressions to properly ventilate the patient. Once cardiac function has been restored, the ventilator may be configured to periodically supply respiratory gases to the patients at known timed intervals. The ventilators of the invention may also be configured to be coupled to various other sensors to monitor various physiologic parameters of the patient during the procedure. For example, such sensors may include oxygen sensors, carbon dioxide sensors, temperature sensors, chest compression force sensors, depth of chest compression sensors, chest compression pressure sensors, pH sensors and the like.

Referring now to FIG. 1, an exemplary embodiment of a ventilation system 10 will be described. System 10 includes a ventilator 12 which is coupled to a pressure responsive valve system 14 by a tube 16. Although not shown, it will be appreciated that valve system 14 will be attached to a coupling mechanism that is configured to couple the ventilator to the patient's airway. For example, coupling mechanisms that may be employed by the invention include facial masks, endotracheal tubes, laryngeal mask airways, and the like. Exemplary valve systems that may be employed include those described in U.S. Pat. Nos. 5,541,420 and 5,692,498, previously incorporated by reference. However, it will be appreciated that other valves may be employed with ventilator 12. As described in greater detail hereinafter, valve system 14 includes a sensor to detect changes in intrathoracic pressure, and more particularly to detect when respiratory gases exit the patient's lungs. This information is transferred to ventilator 12 which counts the number of chest compressions and automatically supplies respiratory gases to the patient after a predetermined number of chest compressions have been counted.

Figure 2:
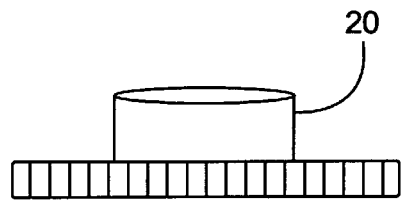
FIG. 2 illustrates an exploded view of the valve of FIG. 1.
Figure 2:
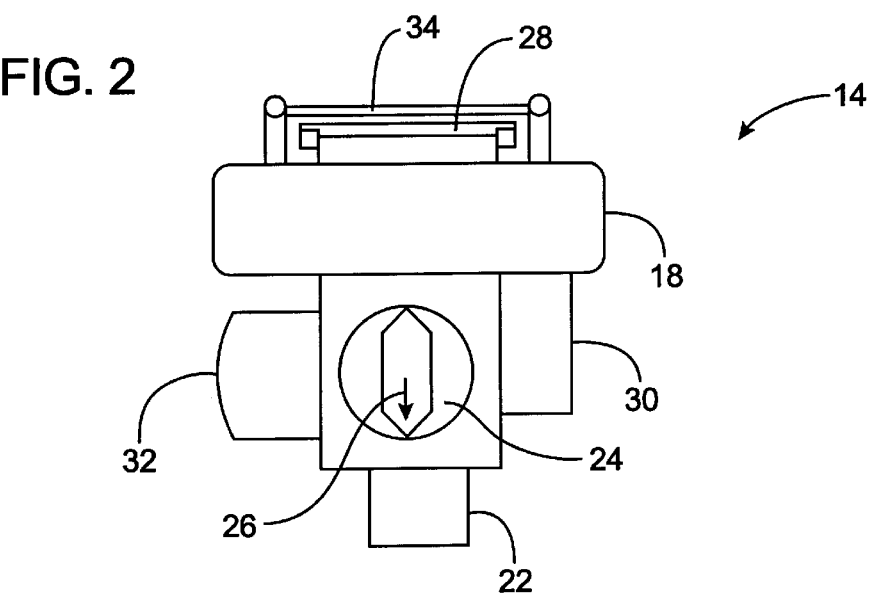

Referring now to FIG. 2, construction of pressure responsive valve system 14 will be described in greater detail. Valve system 14 comprises a housing 18 having an inlet end 20 and an outlet end 22. A flow control valve 24 is disposed in housing 18 to control the flow of air or respiratory gases within housing 18. When an arrow 26 is aligned with inlet end 20 and outlet end 22, the flow of respiratory gases through housing 18 is as follows. When respiratory gases are forced from patient's lungs, the respiratory gases are free to flow through outlet end 22, through housing 18 and out inlet end 20. As respiratory gases flow through housing 18, a diaphragm 28 is lifted to allow passage of the respiratory gases through inlet end 20 as illustrated generally in FIG. 2B. Similarly, when respiratory gases are forced through inlet end 20 (such as when a volume of respiratory gases is supplied from ventilator 12), diaphragm 28 is lifted to allow the respiratory gases to flow through outlet end 22.

Valve system 14 further includes a pressure responsive valve (not shown) within a side intake 32. To increase the magnitude and extent of negative intrathoracic pressure within the patient during the decompression phase of CPR, the pressure responsive valve within side intake 32 is configured to open only after a threshold negative intrathoracic pressure level is exceeded. In this way, respiratory gases are prevented from flowing through housing 18 by diaphragm 28 during the decompression phase. Hence, the only way for respiratory gases to enter into the patient's lungs (if ventilations are not provided) is through the pressure responsive valve inside intake 32 similar to the embodiments described in U.S. Pat. No. 5,692,498, previously incorporated by reference.

In the event that the patient begins spontaneous breathing, flow control valve 24 may be turned 90 degrees clockwise to align arrow 26 with a second side intake 30 which establishes an air passage between side intake 30 and outlet end 22. In this way, the patient may freely breathe through housing 18.

Figure 2A:
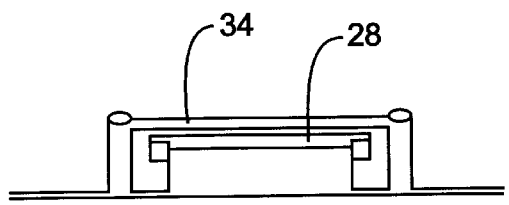
FIG. 2A illustrates a diaphragm of the valve of FIG. 2 without expiratory pressure being applied.
Figure 2B:
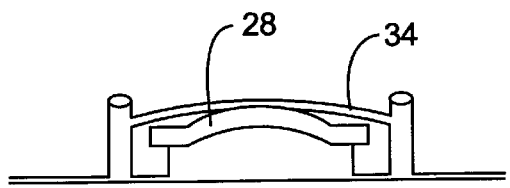
FIG. 2B illustrates the diaphragm of FIG. 2A with expiratory pressure being applied to deflect a strain gauge according to the invention.

Referring now to FIGS. 2A and 2B, sensing of airflow between inlet end 20 and outlet end 22 will be described. Disposed across housing 18 just above diaphragm 28 is a strain gauge 34. In FIG. 2A, diaphragm 28 is shown in a state experienced when expiratory pressure is not being applied. In FIG. 2B, expiratory pressure is being applied as illustrated by the arrows which causes diaphragm 28 to lift and thus deflect strain gauge 34. When strain gauge 34 is deflected, it will be stretched within its elastic limit, causing a change in resistance in the material used to construct strain gauge 34. Such a change in resistance may be detected and used as an indicator that the intrathoracic pressure within the patient's chest has changed. In turn, such information may he used as an indicator that a chest compression has occurred. The construction of such strain gauges is well known within the art, and employ the use of materials such as constantan, nickel, silicon, germanium, and the like.

Preferably, a Wheatstone-bridge (not shown) is included within ventilator 12 to measure the change of resistance of strain gauge 34 when deflected by diaphragm 28. Use of strain gauge 34 in combination with a Wheatstone-bridge is particularly advantageous in that the sensitivity of system 10 may be precisely controlled to accommodate patients having a variety of thoracic morphologies. Although the sensor that is employed to detect airflow through housing 18 is a strain gauge 34, it will be appreciated that other sensors may be provided, including photodiodes, other optical sensors, pressure sensors, piezoelectric sensors, capacitative sensors, and the like. Further, other types of sensors may be employed to detect airflow through the housing (rather than deflection of diaphragm 28), including pressure sensors, spirometers, thermistors, pneumotachometers, captometers, and the like.

Figure 3:
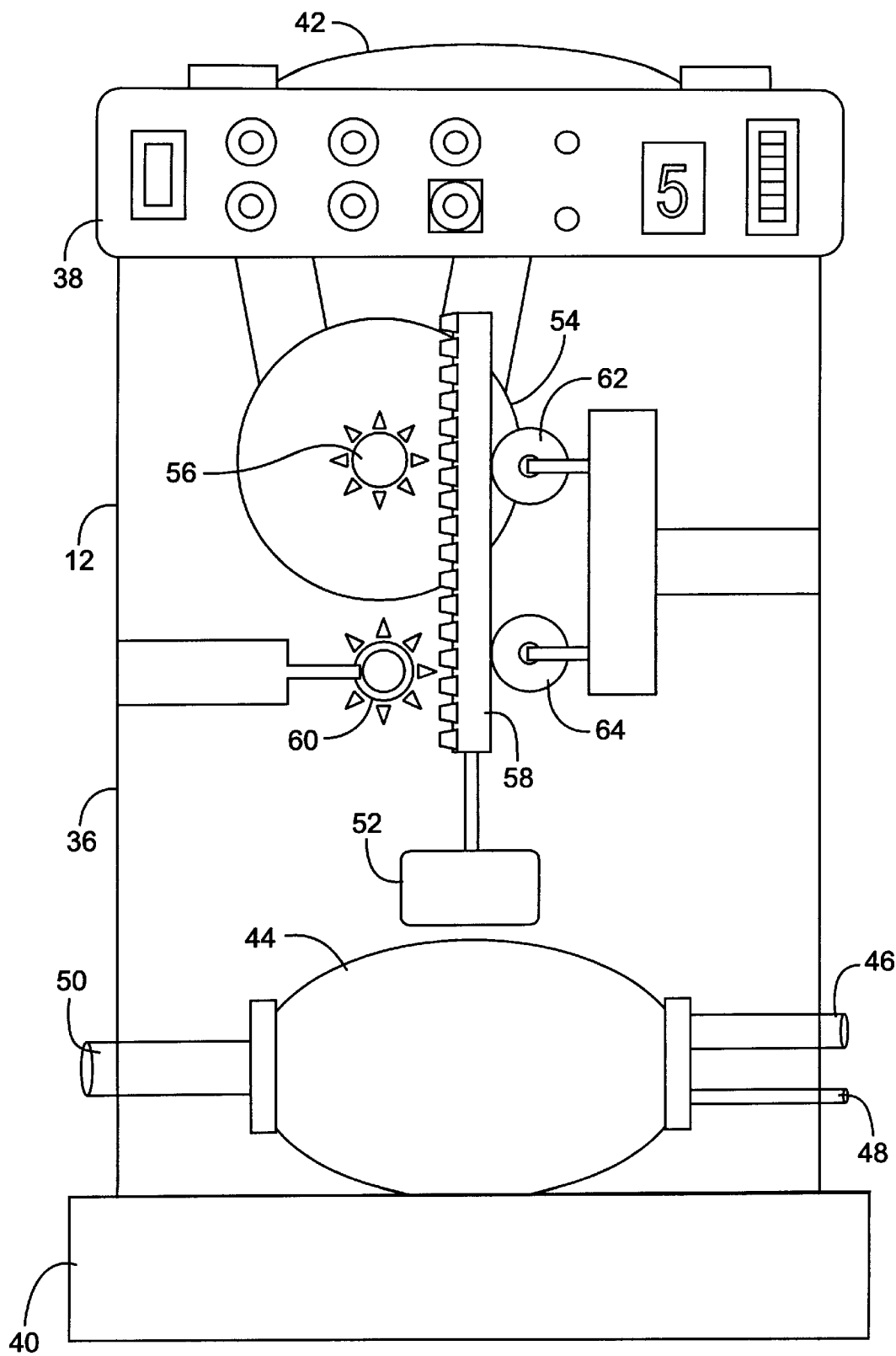
FIG. 3 is a schematic view of the interior of the ventilator of FIG. 1 showing a rack and pinion that is employed to move a plunger against a compressible bag to deliver inspiratory gases through the valve according to the invention.

Referring now to FIG. 3, construction of ventilator 12 will be described in greater detail. Ventilator 12 comprises a housing 36 having a control panel 38 and a compartment 40 which holds a rechargeable battery. Construction of control panel 38 will be described in greater detail hereinafter with reference to FIG. 5. Conveniently, a handle 42 is provided to facilitate transport of ventilator 12.

Disposed in housing 36 is a compressible bag 44 which is coupled at one end to a pair of input ports 46 and 48, which are employed to supply various respiratory gases to compressible bag 44. Merely by way of example, input port 46 may be coupled to an ambient air source while input port 48 is coupled to an oxygen source. Coupled to the other end of compressible bag 44 is an output port 50 through which inspiratory gases are supplied to the patient. As illustrated in FIG. 1, output port 50 is coupled to tube 16. Ventilator 12 includes a plunger 52 which is employed to compress bag 44. Plunger 52 is moved up and down by stepping motor 54 which is coupled to a source pinion 56. Plunger 52 is coupled to a rack 58 which engages source pinion 56 to move plunger 52 up and down depending on the direction of rotation of stepping motor 54. Conveniently, a linear pinion 60 and ball bearing roller 62 and 64 are employed to keep rack 58 coupled to source pinion 56 during operation of stepping motor 54. With such a configuration, stepping motor 54 may be configured to rotate source pinion 56 in a clockwise direction to move plunger 52 downward until bag 44 is compressed. After compression, stepping motor 54 is reversed causing source pinion 56 to rotate in a counter-clockwise direction, thereby lifting plunger 52. Hence, by coupling plunger 52 to stepping motor 54, the amount of compression of bag 44 may be precisely controlled. In this way, a precise volume of respiratory gases may be supplied to the patient during each actuation of ventilator 12.

Figure 3A:
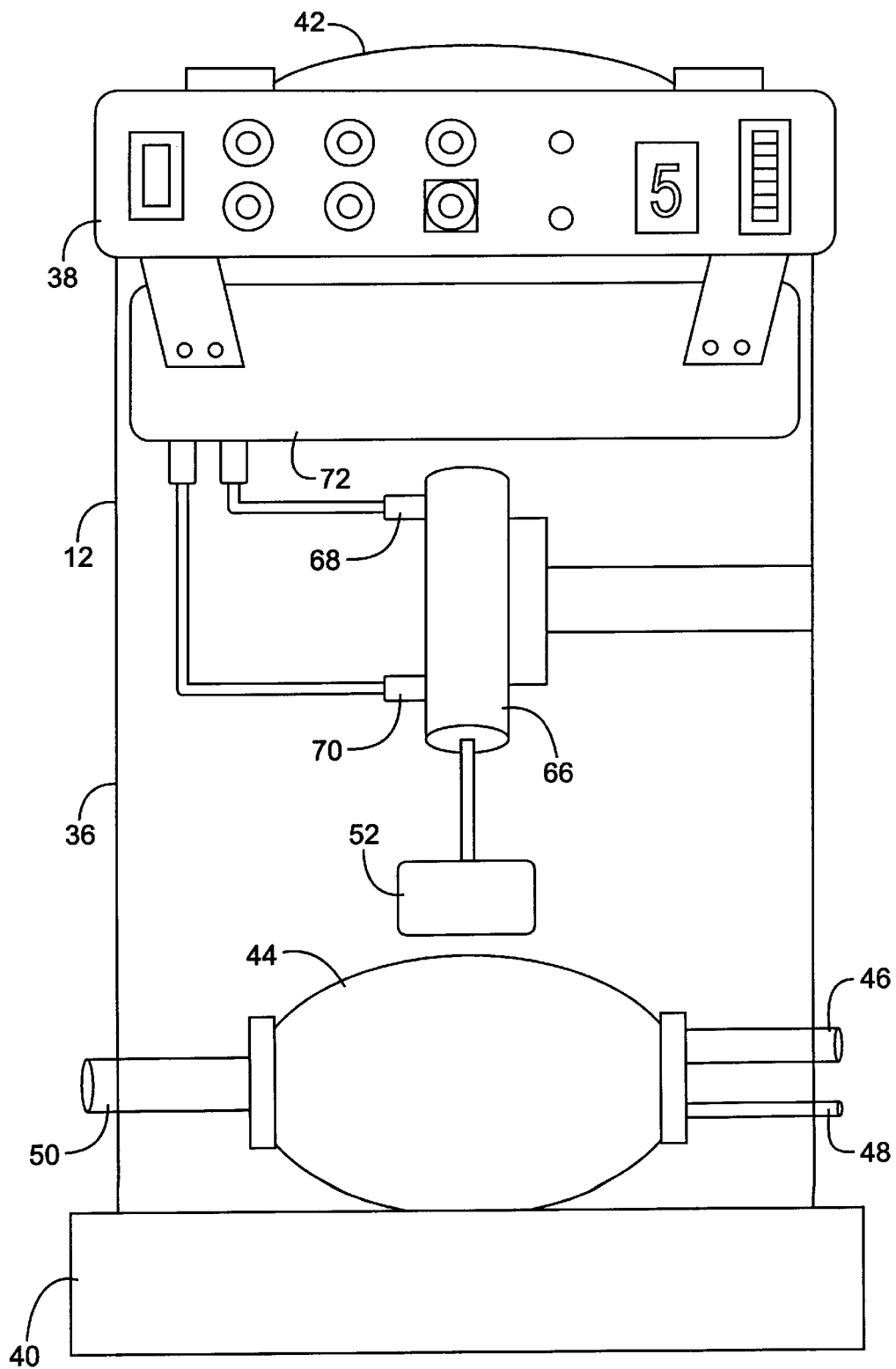
FIG. 3A illustrates the ventilator of FIG. 1 having an air cylinder and plunger to compress the compressible bag according to the invention.

Referring to FIG. 3A, an alternative mechanism for moving plunger 52 against bag 44 will be described. Plunger 52 is coupled to an air cylinder 66 having an inlet port 68 and an outlet port 70. Ports 68 and 70 are in turn coupled to a compressed air tank 72. When inlet port 68 is opened and outlet port 70 is closed, compressed air from tank 72 moves plunger 52 downward to compress bag 44. To lift plunger 52, inlet port 68 is closed and outlet port 70 is opened. Similar to the embodiment of FIG. 3, movement of plunger 52 may be precisely controlled to precisely control the volume of inspiratory gas that is delivered to the patient. A variety of other mechanisms may be employed to compress bag 44 including caliper arms, cams, and the like. Further, it will be appreciated that other mechanisms may be employed to produce a precise volume of inspiratory gases, such as a piston that is slidable within a cylinder.

Figure 4A:
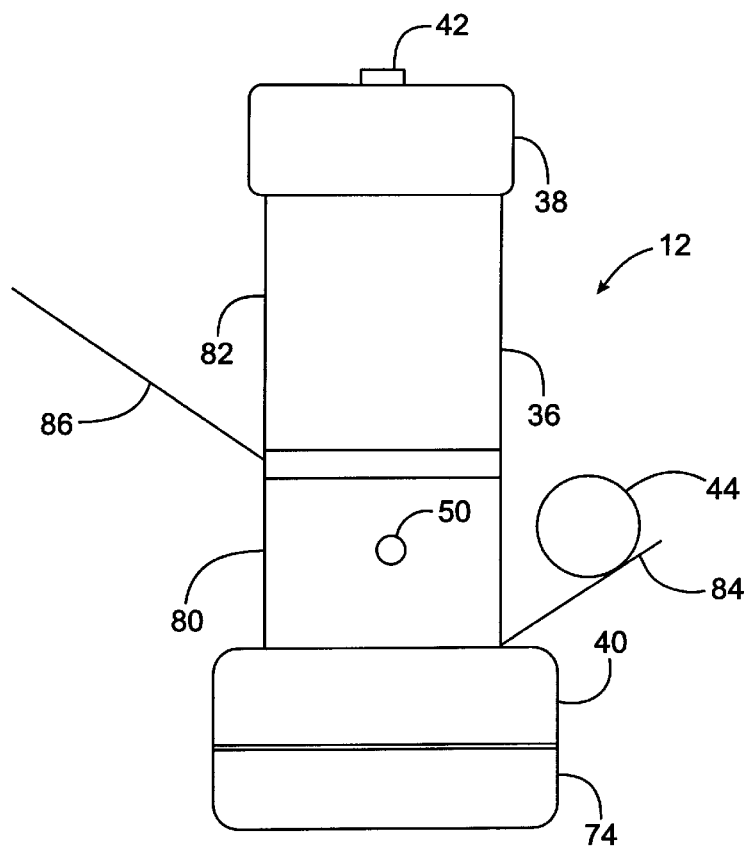
FIG. 4A is a side view of the ventilator of FIG. 1 illustrating a circuit board and motor or air cylinder access compartment and a compressible bag detach compartment.
Figure 4B:
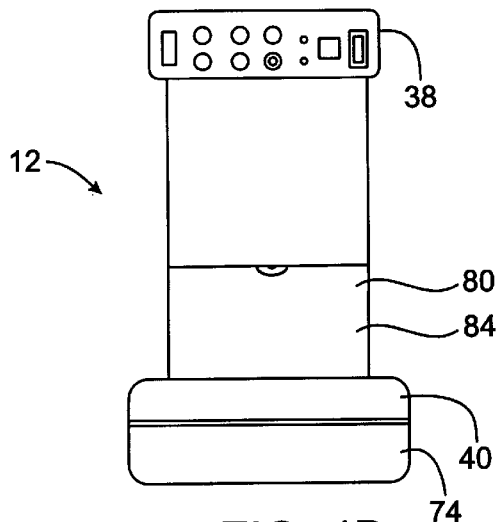
FIG. 4B is a front view of the ventilator of FIG. 1.
Figure 4C:
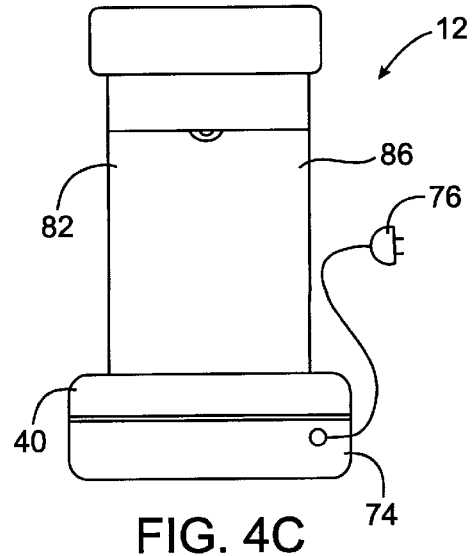
FIG. 4C is a rear view of the ventilator of FIG. 1.

Referring now to FIGS. 4A–4C, other features of ventilator 12 will be described. In FIGS. 4A–4C, battery compartment 40 is coupled to a power supply base 74. Battery compartment 40 preferably includes a rechargeable battery, such as a nickel-cadmium (NiCd) battery. The NiCd battery is recharged by docking battery compartment 40 to power supply base 74. As illustrated in FIG. 4C, power supply base 74 includes an electrical plug 76 which may be plugged into a conventional power source, such as a 110 volt ac outlet, to provide power to power supply base 74. When battery compartment 40 is coupled to power supply base 74, and a power switch 78 on control panel 38 (see FIG. 5) is placed in the "off" position, ventilator 12 is in the recharge mode which recharges the NiCd battery. When ventilator 12 is coupled to power supply base 74 and power switch 78 is placed in the "on" position, power supply base 74 converts alternating current from plug 76 to direct current which is supplied to ventilator 12. When ventilator 12 is uncoupled from power supply base 74 and power switch 78 is placed in the "on" position, ventilator 12 will operate from power supplied by the NiCd battery.

One important feature of ventilation system 10 is that the rechargeable battery may be recharged when not in use simply by coupling battery compartment 40 with power supply base 74 and placing power switch 78 in the "off" position. This allows the rechargeable battery to be charged and fully functional for remote emergency operations.

Housing 36 is preferably constructed of a durable non-metallic material that is capable of withstanding diverse temperature ranges. Exemplary materials include plastics, other durable polymers, and the like. The housing material is preferable waterproof and noncorrosive to enable to withstand various regional climates. In this way, ventilation system 10 will be useful in a wide variety of locations where emergency operations may be performed.

As best shown in FIG. 4A, ventilator 12 includes a compressible bag compartment 80 and a circuit board and motor drive compartment 82. Doors 84 and 86 are provided to allow access into compartments 80 and 82, respectively. As shown in FIG. 4A, compressible bag 44 is detachable from ports 46, 48 and 50 (see FIG. 1). In this way, bag 44 may be removed from ventilator 12 and used manually in connection with valve system 14. Such an arrangement may be useful during situations where ventilation system 10 is used remotely and the rechargeable battery has been depleted. In such a case, bag 44 is simply removed from compartment 80 and attached to valve system 14 which in turn is coupled to the patient's air way. Bag 44 is then manually squeezed when ventilation is needed. Door 86 may be opened to expose the electrical components within ventilator 12 as well as to expose the mechanical components employed to move plunger 52 (see FIG. 3).

Figure 5:
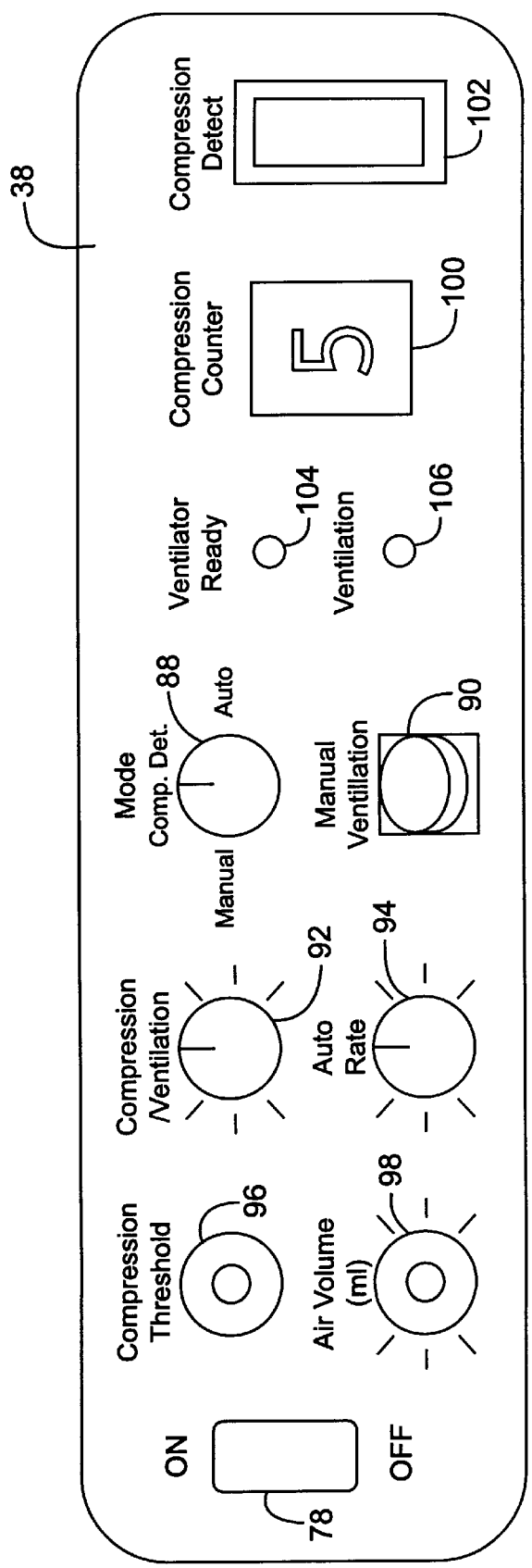
FIG. 5 illustrates a control panel of the ventilator of FIG. 1.

Referring now to FIG. 5, control panel 38 will be described in greater detail. As previously described, control panel 38 includes power switch 78 which is moved between and "on" position and an "off" position. When in the "on" position, electrical power is supplied to the various components of system 10. Control panel 38 further includes a mode control 88 which may be moved between three positions to place ventilation system 10 in a manual mode, a compression detection mode or an automatic mode. When in the manual mode, a user may manually ventilate the patient at any desired ventilation interval by manually pushing a manual ventilation switch 90. When manual ventilation switch 90 is pushed, a volume of air or a respiratory gas is supplied to the patient through inspiratory gas port 50 (see FIG. 4A).

When in the compression detect mode, ventilation system 10 is configured to automatically detect and count the number of chest compressions. Ventilator 12 then automatically ventilates the patient through inspiratory gas port 50 at a preselected compression to ventilation ratio. This ratio may be adjusted by moving a compression/ventilation control 92. By way of example, compression/ventilation control 92 may be moved between ratios in the range from about 2:1 to about 10:1 as determined by the rescuer.

In the automatic ventilation mode, the rescuer is able to automatically ventilate the patient using ventilator 12 as a standard ventilator when CPR is not being performed. The ventilation rate is adjustable in units of breaths per minute via an auto rate control 94. For example, auto rate control 94 may be employed to supply ventilations at rates in the range from about from about 8 to about 30 breaths per minute. The automatic ventilation mode is particularly advantageous when cardiopulmonary function has been restored but the patient still requires ventilation.

Control panel 38 further includes a compression threshold control 96 which may be adjusted to adjust the sensitivity of the strain gauge mechanism housed within ventilator 12 as previously described. In this way, the sensitivity may be adjusted to accommodate various levels of intrathoracic expiratory pressures during CPR chest compressions. The threshold is adjusted by operating compression threshold control 96 which allows for maximum sensitivity without signal saturation to accurately detect changes in intrathoracic pressure. Compression threshold control 96 is a 20-turn, 10,000 Ohm potentiometer that controls the level of the signal received from the transducer prior to being sent to the signal detection amplifying circuit.

Control panel 38 still further includes an air volume control 98 which is employed to adjust the volume of air or respiratory gases inspired to the patient. Air volume control 98 may be manually adjusted to accommodate a diverse range of lung capacities. As previously described, the precise amount of air or gases are delivered to the patient by use of plunger 52 in combination with compressible bag 44. In one alternatively, control 98 may also be employed to control the pressure at which the respiratory gases inspired to the patient.

Other features of control panel 38 include a compression counter display 100 which allows the rescuer to view the cumulative number of compressions. Compression counter display 100 may be configured to count the total number of chest compressions or the number of chest compressions between each ventilation. A compression detect display 102 is provided to allow the viewer to visualize the compression threshold sensitivity. Display 102 reflects the signal level from the transducer amplifying circuit, and preferably comprises a bar-graph LED display that grossly represents the force of compression, i.e., the greater the applied force, the more LEDs that are illuminated.

When power switch 78 is placed in the on position, power is available to operate ventilator 12. Optionally, a ventilator ready display 104 may be provided which comprises a red LED. Ventilation ready display is provided to inform the rescuer that ventilation is about to occur. For example, if mode control 88 is set to the compression detection mode, and compression/ventilation control 92 is set to 5:1 (1 breath for every 5 compressions), ventilator ready display 104 will illuminate at the fourth chest compression. After the fifth compression has been detected, ventilator ready display 104 will be turned off. A ventilation display 106 is lighted each time a ventilation is administered. Preferably, ventilation display 106 comprises an LED which is illuminated green when actuated.

Figure 6:
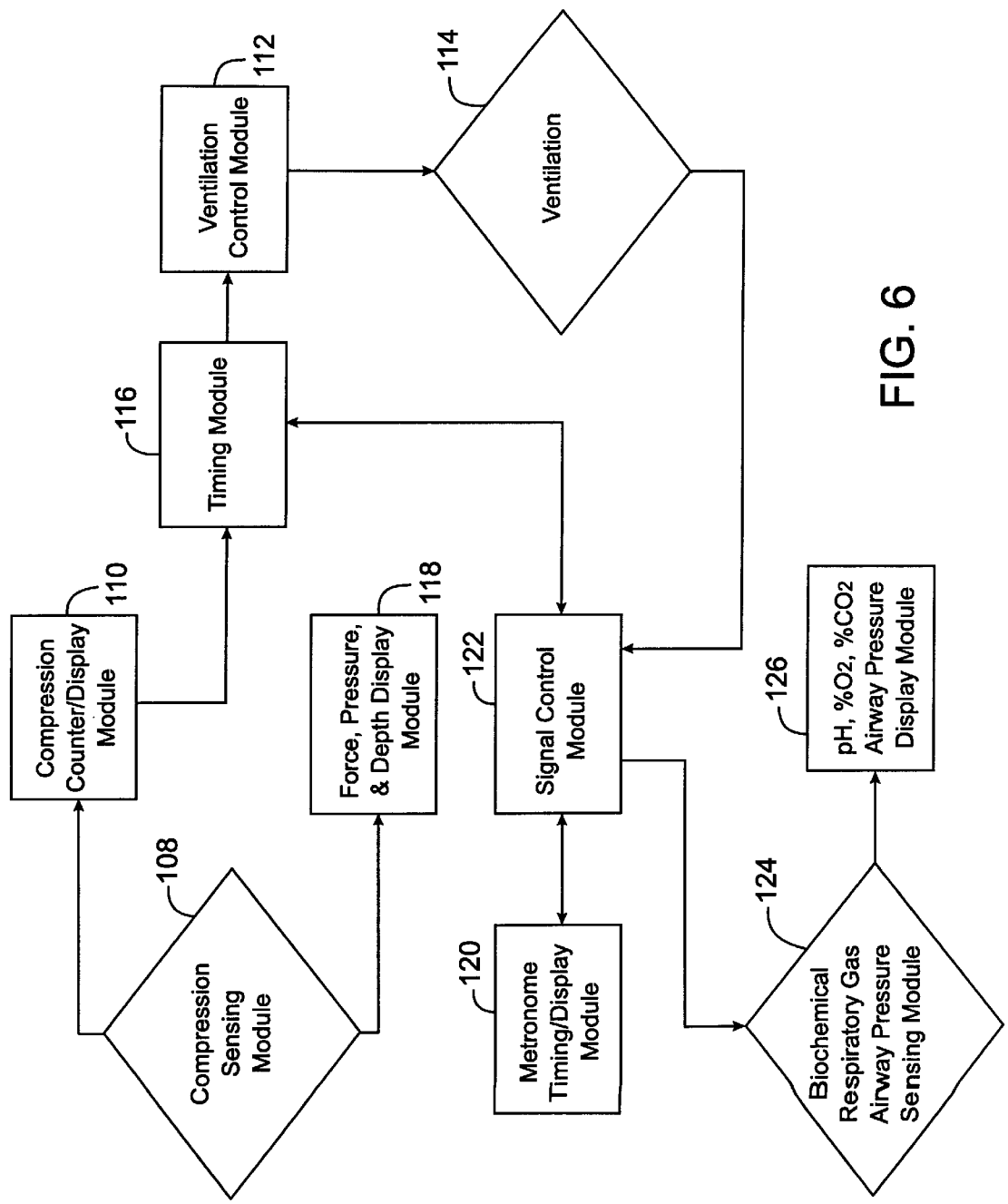
FIG. 6 is a schematic diagram of the circuitry of the ventilator of FIG. 1.

Referring now to FIG. 6, a schematic of the circuitry employed within ventilation system 10 will be described. The circuitry includes a compression sensing module 108 which is coupled to the strain gauge that in turn is disposed in pressure responsive valve system 14. As previously described, compression sensing module 108 preferably includes a Wheatstone-bridge to detect changes in the resistivity of the strain gauge during chest compressions. The compression sensing module 108 is coupled to a compression counter/display module 110. Module 110 counts the number of compressions sensed by module 108 and optionally displays them on compression counter display 100 on display panel 38 (see FIG. 5).

The circuitry further includes a ventilation control module 112 which includes air volume control 98 and which is employed to actuate the mechanical components employed to compress bag 44 (see FIG. 3). These components are illustrated schematically as block 114 in FIG. 6. More specifically, control 98 comprises a 1-turn, 10,000 Ohm potentiometer that controls the rate of a capacitor timing circuit. This circuit in essence controls the duration that plunger 52 compresses bag 44. Since the speed of plunger 52 is internally set at a constant level, adjusting air volume control 98 controls how long plunger 52 is actuated. The time duration of plunger activation represents the linear distance the plunger will travel into bag 44. The distance of plunger 52 into bag 44 represents the volume of respiratory gases supplied to the patient.

Ventilation control module 112 is coupled to mode control 88 of control panel 38 (see FIG. 5). When mode control 88 is in the compression detect mode, module 112 will send a signal to actuate ventilation after a predetermined number of compressions have been counted by module 110. Ventilation control module 112 is further coupled to compression/ventilation control 92 so that ventilation control module 112 will know the number of compressions that must be performed before a signal is sent to actuate ventilation.

Also coupled to ventilation control module 112 is a timing module 116 which provides information to ventilation control module 112 regarding the timing of ventilations when mode control 88 is in the automatic ventilation mode. Timing module 116 is coupled to auto rate control 94 (see FIG. 5) so that information may be provided regarding the rate at which automatic ventilations are to be performed. Ventilation control module 112 is further coupled to manual ventilation switch 90 (see FIG. 5) so that when switch 90 is pressed, a signal may be sent to allow for manual ventilation to be performed.

The circuitry further includes a force, pressure, and depth display module 118 which may be coupled to various force, pressure, and depth sensors. In this way, various characteristics of chest compression may be monitored. For example, ventilation system 10 may measure the force at which chest compressions are being performed, the pressure being applied to the chest, and the depth of chest compression. Optionally, such information may be displayed on control panel 38 (see FIG. 5). This display may be in the form of an LED bar graph or numerically display a measured value, i.e. in pounds, inches, etc. Optionally, the circuitry may also include a metronome/timing display module 120. Module 120 is preferably configured to visually display and produce audible signals at regular intervals to assist the rescuer in performing regular chest compressions.

The circuitry further includes a signal control module 122 which is used to control logic circuitry that controls timing and duration of actuation between other modules, i.e. module 122 serves as a main module to control the other modules.

Coupled to module 122 is a biochemical, respiratory gas, airway pressure sensing module 124. Module 124 is employed to allow various sensors to be coupled to ventilator 12 to provide feedback regarding various physiologic characteristics. For example, sensors such as pressure sensors, oxygen sensors, carbon dioxide sensors, temperature sensors, pH sensors and the like may be coupled to module 124. Use of a pressure sensor is advantageous in that the pressure in the patient's airway may be sensed. In this way, information regarding the pressure in the patient's airway may be employed to control the proper volume of respiratory gases delivered to the patient, to provide positive pressure breaths with the patient's spontaneous ventilatory pattern, or to wean the patient from ventilatory assist to independent breathing as previously described. Optionally, a pH, oxygen and carbon dioxide airway pressure display module 126 may be coupled to module 124 and included on control panel 38 to visually display various physiologic characteristics of the patient, including the pressure in the patient's airway.

Compression sensing module 108 is coupled to compression detect display 102 to visually display the strength of the signal being detected by module 108. Compression sensing module 108 includes compression threshold control 96 as previously described. By adjusting control 96, the sensitivity of the compression detect display 102 may be modified. For example, display 102 may illuminate one LED bar when no compressions are being performed and 5 to 10 LED bars which a chest compression is applied.

As one example, prior to the initiation of CPR, and with the ventilation system connected to the patient, the rescuer adjusts compression threshold control 96 to illuminate only one LED bar on compression detect display 102. This essentially sets the compression sensing circuitry in module 108 to represent zero force applied to the chest. Once compressions begin, the rescuer may monitor display 102 to "grossly" verify that an appropriate amount of force has been applied during chest compressions by observing that 5 to 10 LED bars on compression detect display 102 are illuminated.

Referring back now to FIG. 1, operation of ventilation system 10 to assist in performing a CPR procedure will be described. Initially, ventilation system 10 is coupled to a patient via a coupling device, such as a facial mask, an endotracheal tube, laryngeal mask airway, and the like. As also illustrated in FIG. 5, power switch is turned to the on position and mode control 88 is placed in the compression detect mode. Compression/ventilation control 92 is adjusted to the desired compression/ventilation ratio. The patient then begins performing CPR as is known in the art. When performing chest compressions, compression detect display 102 will light and grossly display the force of compression each time a compression is detected. Further, compression counter display 100 will display the number of chest compressions. When the preset number of chest compressions have been detected, ventilator 102 supplies a volume of respiratory gases to the patient through valve system 14 and counter display 100 is reset to zero. The volume of respiratory gases supplied are controlled by air volume control 98. If desired, mode control 88 may be placed in the manual mode so that ventilations may be manually provided to the patient by depressing manual ventilation switch 90. In another option, bag 44 may be removed from ventilator 12 and coupled to valve system 14 so that ventilations may be manually provided to the patient by having the rescuer manually squeeze bag 44.

If the patient begins spontaneous breathing, flow control valve 24 (see FIG. 2) may be adjusted so that air may freely flow through valve system 14 to the patient's lungs. During times when CPR is not being performed and it is still desired to ventilate the patient, mode control 88 may be placed in the automatic mode where ventilations will be supplied to the patient at a rate determined by control 94 and volume determined by control 98.

Since ventilator 112 has its own rechargeable battery, ventilation system 10 may be used remotely to facilitate its use in medical emergencies. Further, by providing a way to sense when chest compressions are being performed, ventilation may be easily coordinated with chest compressions without requiring the rescuer to concentrate on counting the number of compressions to ensure that regular ventilations are being supplied to the patient.

Figure 7:
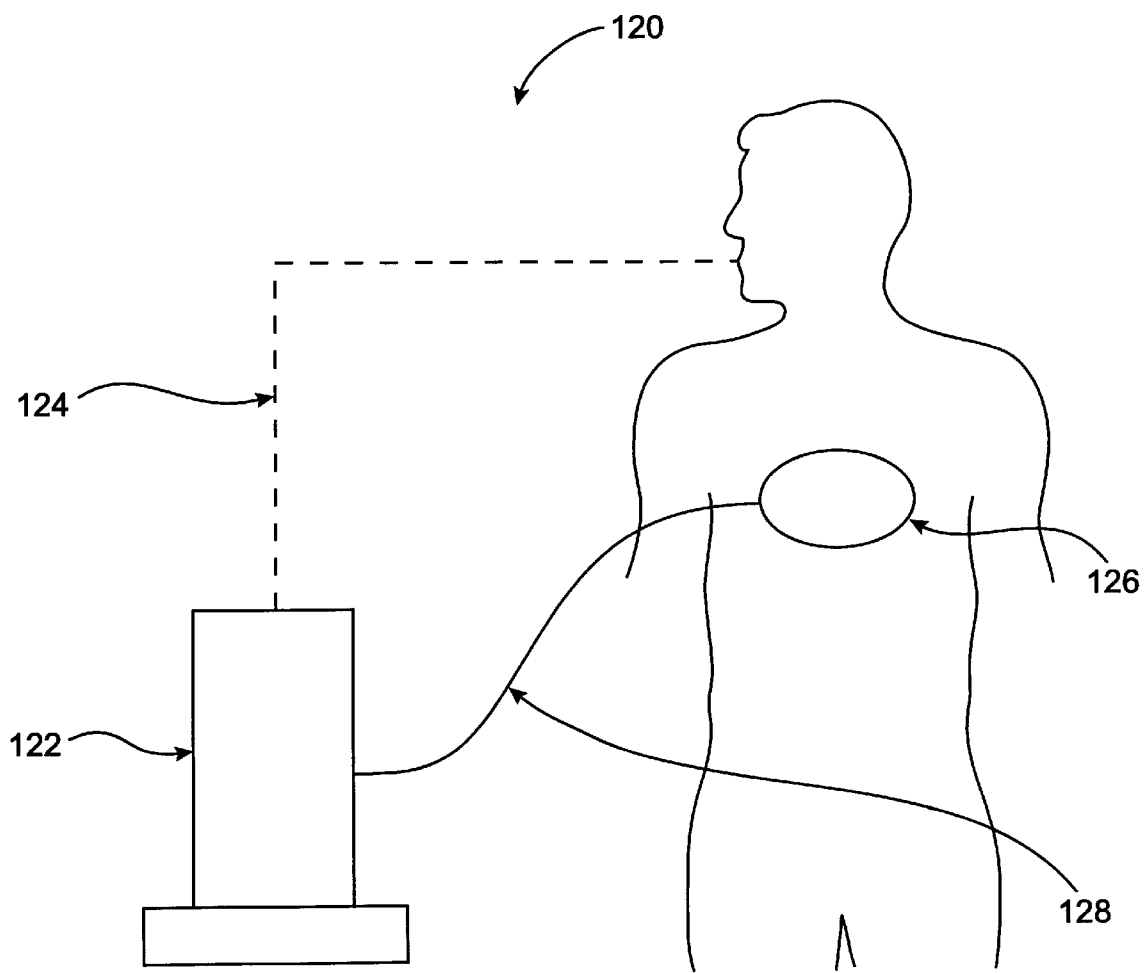
FIG. 7 is a schematic diagram of an alternative system for detecting chest compressions according to the invention.

FIG. 7 illustrates an alternative ventilation system 120 which includes a ventilator 122 which is similar to ventilator 12 as previously described. Ventilator 122 is coupled to a patient by an airway 124. Also coupled to a ventilator 122 is a compression pad 126. Disposed in compression pad 126 is a strain gauge or load cell. In turn, these elements are coupled to ventilator 122 by a two conductor coaxial cable 128. Compression pad 126 is placed over the patient's sternum so that when the patient's chest is compressed (either manually or using an automated compression mechanism), the strain gauge or load cell generates a signal which is transmitted via cable 128 to the ventilator control circuitry in ventilator 122. In this way, chest compressions may be directly sensed. Ventilator 122 is then employed to periodically supply respiratory gases to the patient via airway 124 in a manner similar to that described in the previous embodiment.

Alternatively, compression pad 126 may be configured to be inflated with a fluid, such as air. With this arrangement, a pressure transducer is employed to detect pressure increases within the air filled compression pad so that chest compressions may be directly sensed. In one embodiment, cable 128 is replaced with a flexible, hollow polyethylene tube which is coupled to a pressure transducer that is housed within ventilator 122. In this way, when the compression pad is compressed, the transducer within ventilator 122 detects the increase in pressure. In turn, signals generated by the pressure transducer are conducted to the ventilator control circuitry. Alternatively, the pressure transducer may be held within the compression pad (or another compression device), to detect an increase in pressure within the pad during chest compressions. A signal of the pressure transducer is then preferably transmitted via a two conductor coaxial cable to the ventilator control circuitry in ventilator 122.

As previously described, it is preferred to prevent respiratory gases from flowing to the patient's lungs during at least a portion of the decompression phase of CPR. Alternative occlusion mechanisms for preventing air from entering into the patient's airway during the decompression phase are illustrated in FIGS. 8A–11B. Such occlusion mechanisms may be coupled to the ventilator circuitry in the ventilators described herein. In this way, the various occlusion mechanisms may be configured to open and close based on information provided by the various sensors when sensing chest compressions. For example, the occlusion mechanisms may be configured to be closed until a specified time period after a chest compression has been detected to insure that sufficient time has passed during the decompression phase. At this point, the occlusion mechanisms are configured to open to allow respiratory gases to flow to the patient's lungs.

Various sensing mechanisms may also be provided to detect when the patient begins spontaneous breathing. In this event, the occlusion mechanisms will be opened to allow the free flow of air into the patient's lungs. Further, the ventilators may be configured to open the various occlusion mechanisms after a predetermined negative intrathoracic pressure level has been met or exceeded. In this way, the opening pressures of the various occlusion mechanisms may be controlled via the ventilator.

Figure 8A:
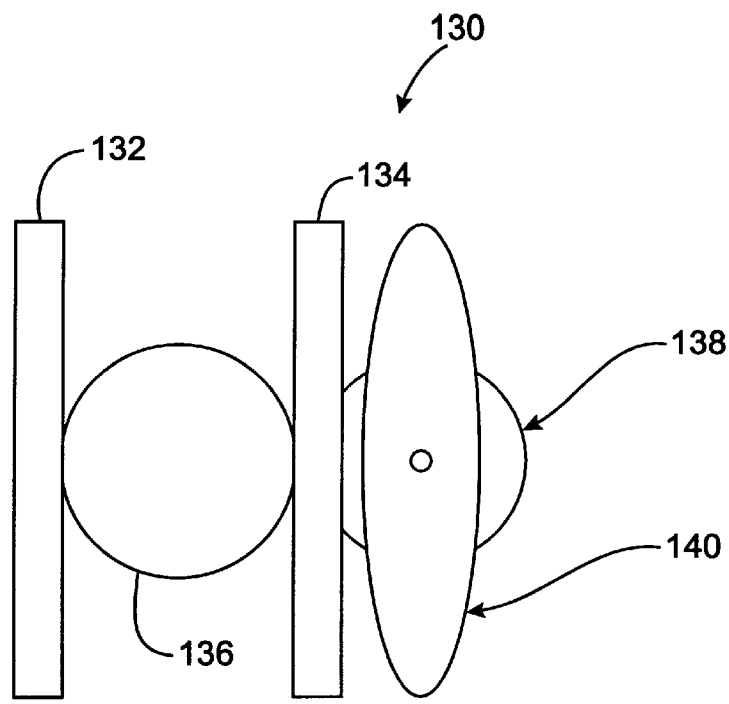
FIG. 8A illustrates a rotary cam wheel airway occlusion mechanism according to the invention.
Figure 8B:
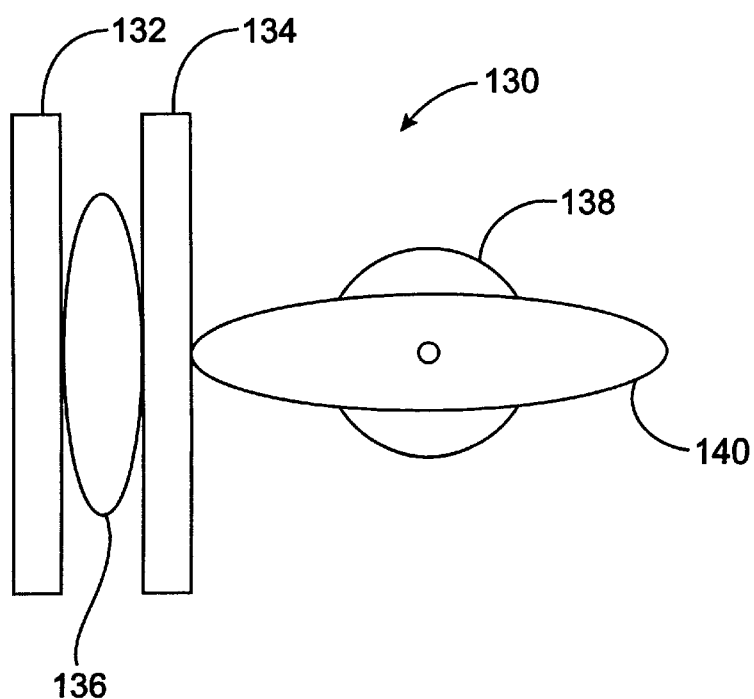
FIG. 8B illustrates the mechanism of FIG. 8A when the rotary cam wheel has been rotated to close an airway lumen.

Referring now to FIGS. 8A and 8B, one embodiment of a rotary cam wheel airway occlusion mechanism 130 will be described. Mechanism 130 comprises a pair of spaced apart occlusion members 132 and 134 which are placed on opposite sides of an airway lumen 136 through which respiratory gases are provided to the patient. A DC stepping motor 138 having a rotary cam wheel 140 is positioned in close proximity to occlusion member 134. As illustrated in FIG. 8B, rotary cam wheel 140 is rotated approximately 90 degrees to force occlusion member 132 against airway lumen 136 until lumen 136 is closed to prevent respiratory gases from flowing through airway lumen 136.

Figure 9A:
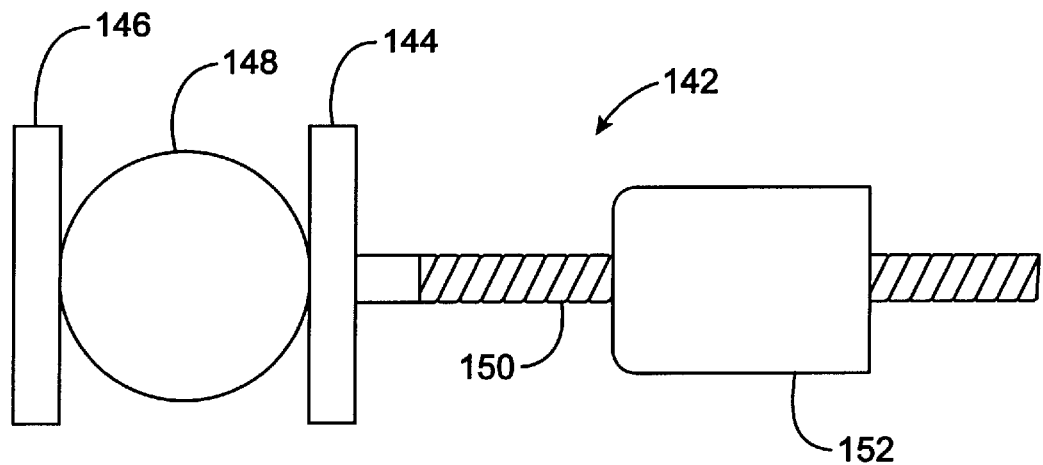
FIG. 9A illustrates a linear actuator occlusion mechanism according to the invention.
Figure 9B:
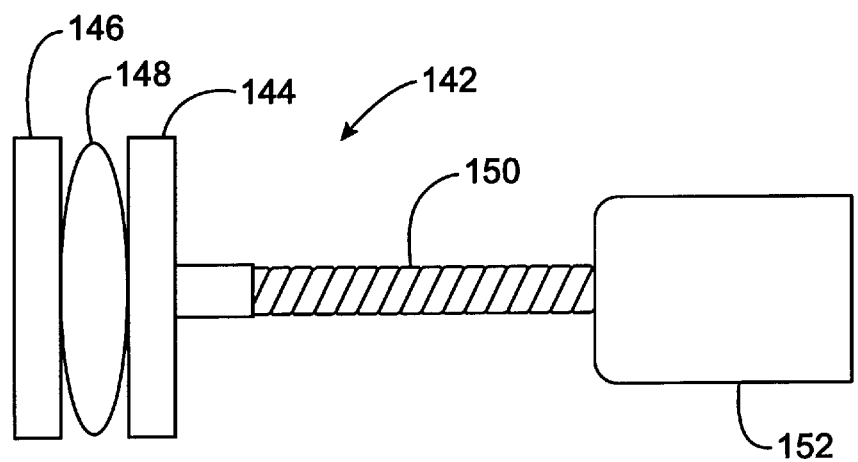
FIG. 9B illustrates the linear actuator occlusion mechanism of FIG. 9A when operated to close an airway lumen according to the invention.

FIGS. 9A and 9B illustrate a linear actuator occlusion mechanism 142. Occlusion mechanism 142 comprises a pair of compression members 144 and 146 that are disposed on opposite sides of an airway lumen 148. Coupled to occlusion member 144 is a lead screw 150 which is translated by a linear actuator 152. As illustrated in FIG. 9B, when linear actuator 152 is actuated, compression member 144 is forced against airway lumen 148 to close airway lumen 148.

Figure 10A:
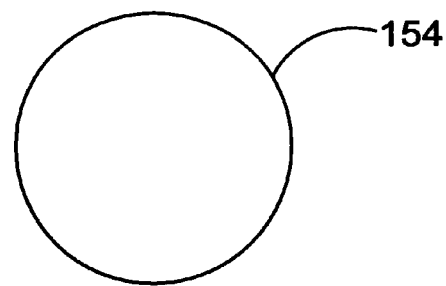
FIG. 10A illustrates a non-occluded airway lumen according to the invention.
Figure 10B:
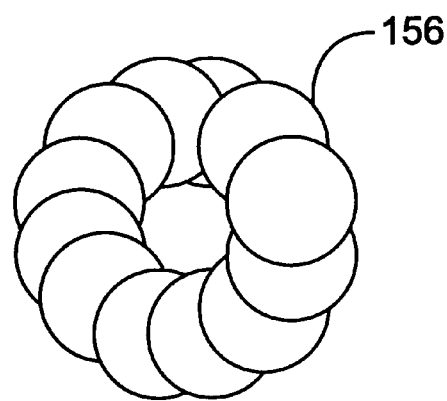
FIG. 10B illustrates the airway lumen of FIG. 10A when occluded with an iris occluding mechanism according to the invention.

FIGS. 10A and 10B illustrate an airway lumen 154 in an open configuration. As shown in FIG. 10B, airway lumen 154 is closed by an iris occluding mechanism 156.

Figure 11A:
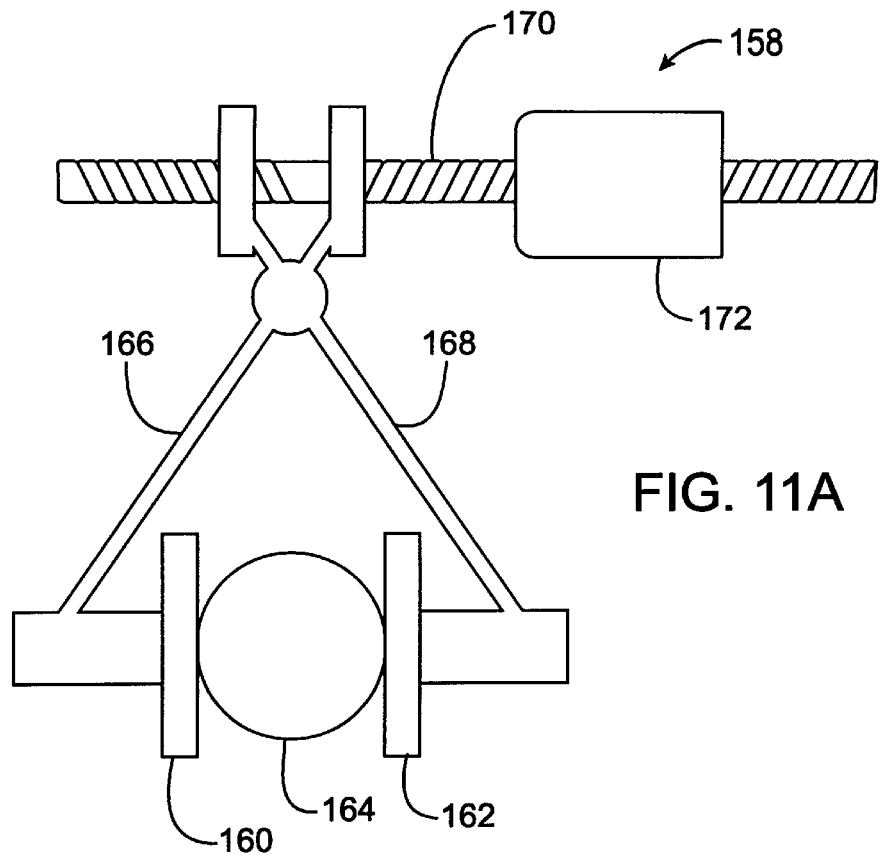
FIG. 11A illustrates a caliper occlusion mechanism according to the invention.
Figure 11B:
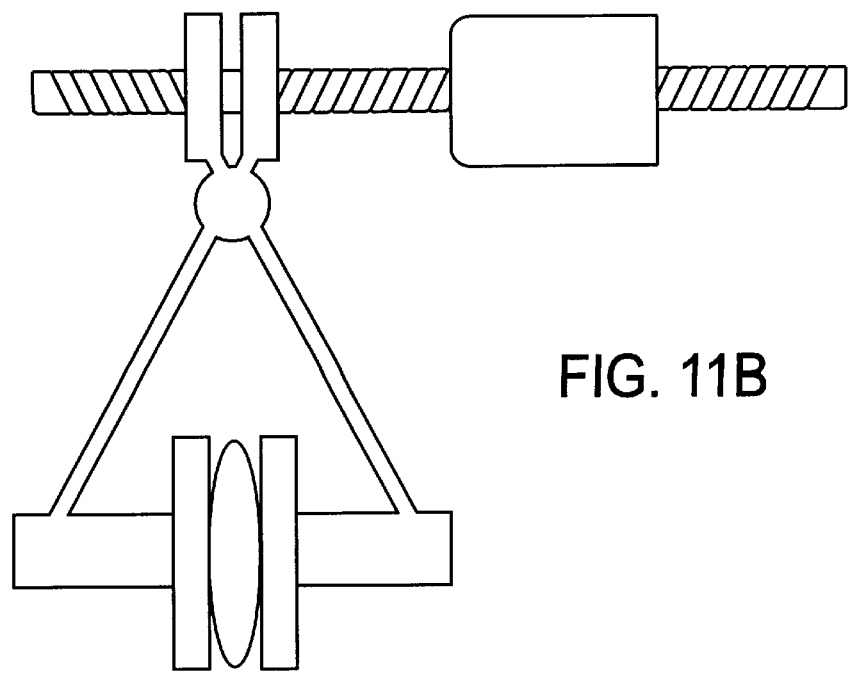
FIG. 11B illustrates the caliper occlusion mechanism of FIG. 11A when operated to close an airway lumen according to the invention.

FIGS. 11A and 11B illustrate a caliper occlusion mechanism 158. Caliper occlusion mechanism 158 includes compression members 160 and 162 that are disposed between airway lumen 164. A pair of caliper arms 166 and 168 are coupled to a lead screw 170. In turn, lead screw 170 is translated by a linear actuator 172. As illustrated in FIG. 11B, when linear actuator 172 is operated, caliper arms 166 and 168 are brought together to force compression members 160 and 162 against airway lumen 164.

Figure 12A:
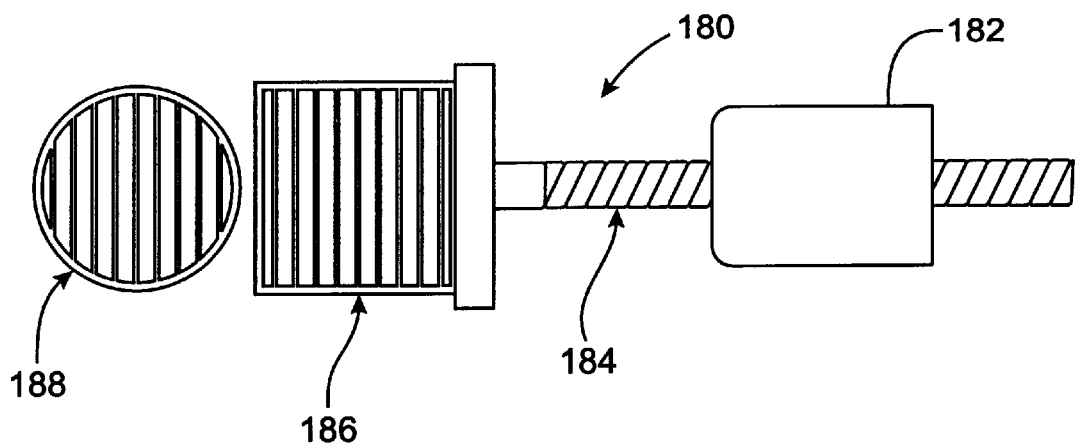
FIG. 12A illustrates a mesh occlusion mechanism according to the invention.
Figure 12B:
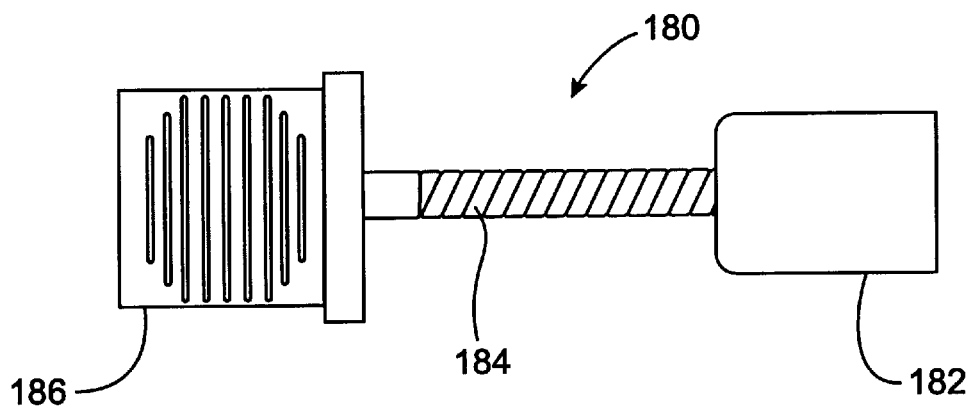
FIG. 12B illustrates the mesh occlusion mechanism of FIG. 12A when operated to close an airway lumen according to the invention.

FIGS. 12A and 12B illustrate a mesh occlusion mechanism 180 which includes a linear actuator 182, a lead screw 184 and an occluding mesh 186. As shown in FIG. 12B, mesh 186 is moved across an airway lumen 188 to occlude the lumen.

Figure 13A:
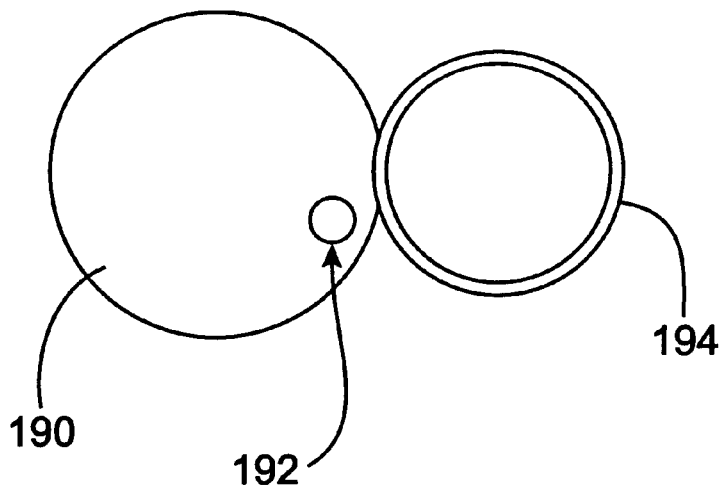
FIG. 13A illustrates a rotatable disc occlusion mechanism according to the invention.
Figure 13B:
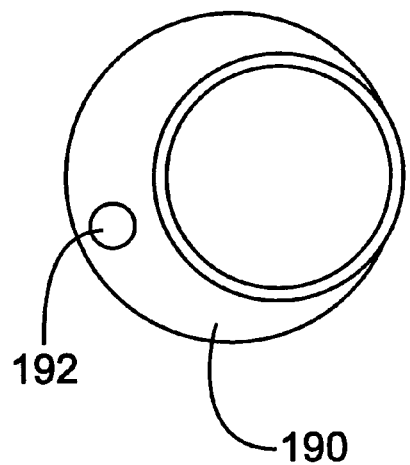
FIG. 13B illustrates the disc of FIG. 13A when rotated to close an airway lumen.

FIGS. 13A and 13B illustrate a disc 190 which is rotatable about an arm 192 to place disc 190 across an airway lumen 194.

The invention has now been described in detail for purposes of clarity of understanding. However it would be appreciated that certain changes and modifications may be practiced within the scope of the append claims. Therefore, the scope and content of the application should be viewed in light of the appended claims as well as the full scope of equivalence to which those claims are entitled.

What is claimed is:

1. A system for ventilating a patient in association with a cardiopulmonary resuscitation procedure, the system comprising:

a ventilator to periodically supply respiratory gases to a patient's lungs;

a sensor to detect chest compressions;

a controller coupled to the sensor, the controller controlling actuation of the ventilator after a predetermined number of chest compressions have been detected by the sensor;

a valve that is adapted to be placed in communication with the patient's airway, the valve being configured to prevent respiratory gases from flowing to the lungs until a threshold negative intrathoracic pressure is exceeded at which time the valve opens to allow the flow of respiratory gases to the lungs, and wherein the controller is configured to open the valve to permit respiratory gases to flow to the lungs once the patient begins spontaneously breathing.

2. A system as in claim 1, wherein the controller is configured to actuate the ventilator to supply respiratory gases to the patient once about every 2 to about 10 chest compressions.

3. A system as in claim 1, wherein the sensor is configured to sense changes in intrathoracic pressure to detect chest compressions.

4. A system as in claim 1, wherein the sensor is disposed to detect the flow of respiratory gases through the valve upon compression of the chest.

5. A system as in claim 4, wherein the sensor comprises a strain gauge which is strained as respiratory gases flow through the valve and deflect a diaphragm, and a resistance sensing circuit to sense a change in resistance of the strain gauge when strained.

6. A system as in claim 4, wherein the sensor is configured to detect an increase in pressure in the patient's airway with each chest compression.

7. A system as in claim 1, further comprising a chest compression member coupled to the controller, and wherein the sensor is disposed to sense when a compressive force is applied to the chest compression member.

8. A system as in claim 7, wherein the chest compression member comprises a chest pad.

9. A system as in claim 1, wherein the sensor comprises an impedance sensor to sense a change in impedance in the chest wall of the patient upon compression of the chest.

10. A system as in claim 1, wherein the ventilator comprises a compressible member and a compression mechanism to compress the compressible member.

11. A system as in claim 1, wherein the valve comprises an occlusion mechanism to prevent respiratory gases from entering the patient's lungs during at least a portion of a decompression phase of the cardiopulmonary resuscitation procedure.

12. A system as in claim 11, wherein the occlusion mechanism comprises an airway and a threshold valve disposed in the airway.

13. A system as in claim 11, wherein the occlusion mechanism comprises an airway and a rotary cam wheel to compress the airway.

14. A system as in claim 11, wherein the occlusion mechanism comprises an airway, and a linear actuator and a compression member to compress the airway.

15. A system as in claim 11, wherein the occlusion mechanism comprises an airway, and a pair of caliper arms to compress the airway.

16. A system as in claim 11, wherein the occlusion mechanism has adjustable operating pressure levels to vary a threshold negative intrathoracic pressure level that must be exceeded before the occlusion mechanism will allow respiratory gases to flow to the patient's lungs.

17. A system as in claim 16, wherein the occlusion mechanism is coupled to the controller which is configured to operate the occlusion mechanism.

18. A system as in claim 1, further comprising a compression mechanism coupled to the controller to compress the chest.

19. A system as in claim 1, further comprising a power supply to supply power to the controller and the ventilator.

20. A system as in claim 1, further comprising at least one feedback sensor coupled to the controller.

21. A system as in claim 20, wherein the feedback sensor is selected from the group of sensors consisting of oxygen sensors, carbon dioxide sensors, temperature sensors, chest compression force sensors, depth of chest compression sensors, chest compression pressure sensors and pH sensors.

22. A system as in claim 1, further comprising a control panel having a mode control to change the operational mode of the ventilator.

23. A system as in claim 22, wherein the mode control includes a compression detect mode where the ventilator is actuated after the predetermined number of chest compressions have been detected by the sensor.

24. A system as in claim 22, wherein the mode control includes a manual ventilation mode, and wherein the control panel includes a manual ventilation switch which is manually actuatable to actuate the ventilator when the mode control is in the manual ventilation mode.

25. A system as in claim 22, wherein the mode control includes an automatic ventilation mode, and wherein the controller is configured to actuate the ventilator at regularly timed intervals when the mode control is in the automatic ventilation mode.

26. A system as in claim 22, wherein the control panel further includes a threshold compression control to vary the sensitivity level of the sensor.

27. A system as in claim 22, wherein the control panel further includes a respiratory gas volume control to control the volume of respiratory gases supplied by the ventilator upon each actuation.

28. A system as in claim 22, wherein the control panel further includes a respiratory gas control to control the pressure of the respiratory gases delivered with each actuation of the ventilator.

29. A system as in claim 22, wherein the control panel further includes a compression counter display to display the number of detected chest compressions, and a compression detect display to display the detection of a chest compression.

30. A system as in claim 22, wherein the control panel includes a compression display to display compression pressures or forces supplied to the chest.

31. A system as in claim 22, wherein the control panel further includes a ventilation indicator to indicate when the ventilator is actuated.

32. A method for performing cardiopulmonary resuscitation, the method comprising:
   repeatedly compressing a patient's chest;
   detecting each chest compression with a sensor that is coupled to a controller;
   periodically ventilating the patient after a predetermined number of chest compressions have been detected;
   preventing respiratory gases from flowing to the lungs with a valve until a threshold negative intrathoracic pressure is exceeded at which time the valve opens to allow the flow of respiratory gases to the lungs; and
   sensing when the patient begins to spontaneously breath, and permitting respiratory gases to flow to the patient's lungs once spontaneous breathing is detected.

33. A method as in claim 32, further comprising ventilating the patient once about every 2 to about 10 chest compressions.

34. A method as in claim 32, further comprising placing a valve in the patient's airway, and wherein the sensing step comprises sensing when respiratory gases flow through the valve upon compression of the chest.

35. A method as in claim 34, further comprising preventing respiratory gases from flowing to the lungs with the valve until a threshold negative intrathoracic pressure is exceeded at which time the valve opens to allow the flow of respiratory gases to the lungs.

36. A method as in claim 32, further comprising sensing changes in intrathoracic pressure to detect chest compressions.

37. A method as in claim 32, further comprising sensing when a force has been applied to the patient's chest to detect chest compressions.

38. A method as in claim 32, further comprising preventing respiratory gases from entering into the patient's lungs during at least a portion of a decompression phase.

39. A method as in claim 38, further comprising varying an intrathoracic pressure level at which respiratory gases are allowed to enter into the patient's lungs during the decompression phase.

40. A method as in claim 32, further comprising manually compressing the patient's chest or providing chest compressions with a compression mechanism coupled to the controller.

41. A method as in claim 32, further comprising mechanically compressing an air bag to ventilate the patient.

42. A method as in claim 41, wherein the air bag is automatically compressed after the predetermined number of chest compressions have been detected.

43. A method as in claim 41, wherein compression of the air bag is manually actuated.

44. A method as in claim 32, further comprising stopping compression of the patient's chest and ventilating the patient at regular intervals.

45. A method as in claim 32, further comprising sensing at least one physiologic parameter while performing chest compressions.

46. A method as in claim 43, wherein the physiologic parameter is selected from the group consisting of oxygen, carbon dioxide, temperature and pH.

47. A method as in claim 45, further comprising visually displaying when each chest compression has been detected.

48. A method as in claim 45, further comprising counting the number of chest compression and displaying the number of counted compressions.

49. A method as in claim 32, further comprising visually displaying an indicator each time the patient is ventilated.

50. A method as in claim 32, further comprising controlling the volume of respiratory gases supplied to the patient by sensing the amount of positive inspiratory pressure supplied to the patient's airway and maintaining the supplied gases at the sensed pressure for a specified time period.

51. A method as in claim 32, further comprising sensing when the patient takes a spontaneous breath and initiating an inspiratory ventilation cycle to assist the patient's breathing.

52. A method as in claim 51, further comprising sensing when the patient begins regular spontaneous breathing and ceasing the inspiratory ventilation cycle.

53. A method as in claim 52, further comprising sensing if the patient stops spontaneous breathing and periodically ventilating the patient after the predetermined number of chest compressions have been detected.

* * * * *